US009662626B2

(12) United States Patent
Yates et al.

(10) Patent No.: US 9,662,626 B2
(45) Date of Patent: May 30, 2017

(54) PHOTOCATALYST AIR PURIFICATION SYSTEM WITH ULTRAVIOLET LIGHT EMITTING DIODES OPERATED WITH A DUTY CYCLE

(71) Applicant: HONEYWELL INTERNATIONAL INC., Morristown, NJ (US)

(72) Inventors: Stephen Yates, South Barrington, IL (US); Bijan F. Hagh, Newport Beach, CA (US); Mark Poling, Springfield, OH (US); Peter M. Michalakos, Arlington Heights, IL (US); Russell W. Johnson, Elmhurst, IL (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 147 days.

(21) Appl. No.: 14/315,043

(22) Filed: Jun. 25, 2014

(65) Prior Publication Data

US 2015/0375187 A1     Dec. 31, 2015

(51) Int. Cl.
   *B64D 13/06*    (2006.01)
   *B01J 8/00*     (2006.01)
   (Continued)

(52) U.S. Cl.
   CPC ............... *B01J 8/008* (2013.01); *A61L 2/00* (2013.01); *A61L 9/00* (2013.01); *A61L 9/205* (2013.01);
   (Continued)

(58) Field of Classification Search
   CPC ............ B01D 2259/4508; B01D 51/00; B01D 2257/708; B01D 2255/802; B64D 13/06;
   (Continued)

(56) References Cited

U.S. PATENT DOCUMENTS 6,358,374 B1 *  3/2002  Obee ................ B01D 53/0415
                                                  204/157.3
6,613,277 B1 *  9/2003  Monagan .............. A61L 9/20
                                                  250/432 R
(Continued)

FOREIGN PATENT DOCUMENTS

JP      04521558 B2    8/2010
JP      2013167424 A   8/2013
(Continued)

OTHER PUBLICATIONS

Chen HW1, Ku Y, Irawan A.; Photodecomposition of O-Cresol by UV-LED/TiO2 Process with Controlled Periodic Illumination; Chemosphere; Sep. 2007; 69(2): 184-190; Epublication Jun. 4, 2007.

(Continued)

*Primary Examiner* — Tien Dinh
*Assistant Examiner* — Vicente Rodriguez
(74) *Attorney, Agent, or Firm* — Shimokaji IP

(57) ABSTRACT

An air purification system includes a photocatalyst on a support disposed to contact airflow through an airflow channel passing across or through the support; an ultraviolet light emitting diode (UV-LED) disposed to emit ultraviolet light onto the photocatalyst, the UV-LED operated at a less than one hundred percent duty cycle, the duty cycle determined at least in part as a function of a desired minimum volatile organic compound conversion rate of air flowing through the airflow channel and a desired maximum by-product concentration of air flowing through an outlet of the airflow channel.

18 Claims, 6 Drawing Sheets

(51) Int. Cl.
*A61L 9/20* (2006.01)
*A61L 2/00* (2006.01)
*A61L 9/00* (2006.01)
*F24F 3/16* (2006.01)

(52) U.S. Cl.
CPC ............. *B64D 13/06* (2013.01); *F24F 3/166* (2013.01); *B01D 2255/802* (2013.01); *B01D 2257/708* (2013.01); *B64D 2013/0637* (2013.01); *B64D 2013/0651* (2013.01); *F24F 2003/1667* (2013.01)

(58) Field of Classification Search
CPC .... B64D 2013/0637; B64D 2013/0651; A61L 9/20; A61L 9/00; A61L 9/02; A61L 9/205; A62B 21/10; F24F 3/166; F24F 2003/1667
USPC ........ 244/118.5; 423/245.1; 422/4, 120, 122
See application file for complete search history.

(56) References Cited

U.S. PATENT DOCUMENTS

| | | | | |
|---|---|---|---|---|
| 6,716,406 | B2* | 4/2004 | Reisfeld | A61L 9/20 422/108 |
| 6,752,957 | B1* | 6/2004 | De Lasa | A61L 2/22 422/186.3 |
| 6,787,782 | B1* | 9/2004 | Krosney | B60H 3/06 250/432 R |
| 7,767,169 | B2* | 8/2010 | Snyder | A61L 9/205 422/121 |
| 2005/0224335 | A1* | 10/2005 | Carmignani | A61L 2/088 204/157.15 |
| 2011/0085933 | A1* | 4/2011 | Mazyck | A61L 9/205 422/4 |
| 2012/0080107 | A1 | 4/2012 | Kruglick | |
| 2013/0034470 | A1 | 2/2013 | Wang et al. | |

FOREIGN PATENT DOCUMENTS

| | | |
|---|---|---|
| JP | 2013192966 A | 9/2013 |
| WO | 2009019388 A1 | 12/2009 |

OTHER PUBLICATIONS

N.L. Nagda, H.E. Rector; A Critical Review of Reported Air Concentrations of Organic Compounds in Aircraft Cabins; Indoor Air; 13; 292-301; Feb. 17, 2003.
Search Report dated Nov. 10, 2015 received in EP Application No. 15170002.8-1602.

* cited by examiner

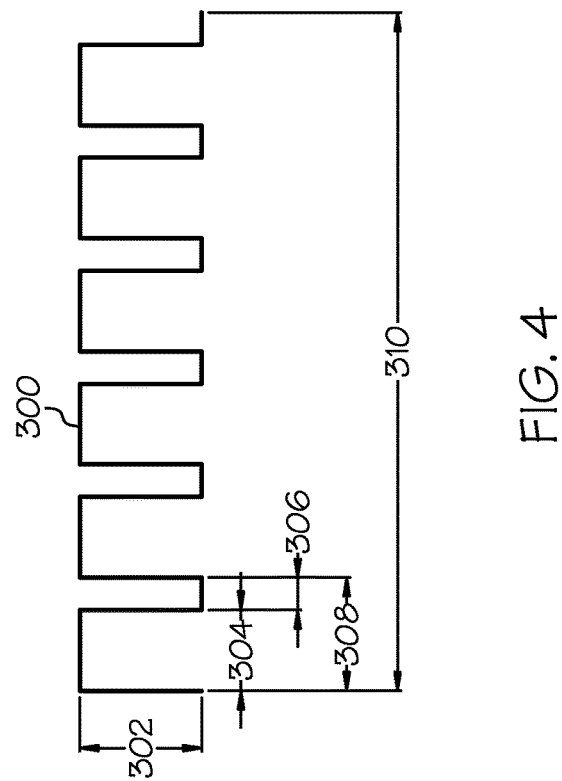
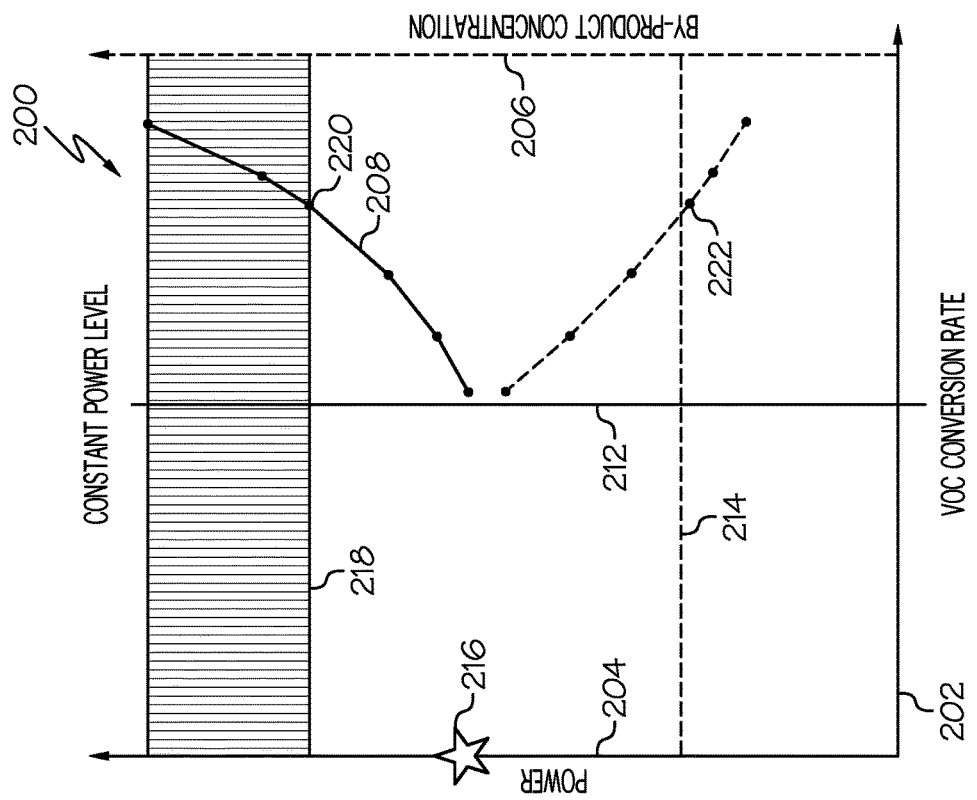
FIG. 4
FIG. 3

PHOTOCATALYST AIR PURIFICATION SYSTEM WITH ULTRAVIOLET LIGHT EMITTING DIODES OPERATED WITH A DUTY CYCLE

BACKGROUND OF THE INVENTION

The present invention generally relates to air purification systems, and more particularly, to an air purification system and method using a photocatalyst and ultraviolet light emitting diodes (UV-LEDS) operated with a duty cycle.

The use of recirculated air may be common within inhabited enclosures. In some cases, airflow may be necessarily recirculated to provide breathable air where air external to the enclosure may not be viable. In other cases, it may be more economical to use recirculated air which has already been adjusted to the correct temperature and humidity. For example, pressurized cabins in aircraft may commonly recirculate a portion of the air rather than try to circulate only external air into the cabin. One result of using recirculated air is that organic contaminants, including volatile organic compounds (VOCs), may increase in concentration to undesirable levels, and may be passed to the inhabitants of the cabin.

One approach to removing contaminants from airflow is to use a photocatalytic air cleaner on airflow. It may be known to use, for example, an array of UV-LEDs to irradiate a photocatalyst in contact with the airflow. Although this may result in removing contaminants from the airflow through an oxidation process, the radiation from the UV-LEDs may also heat the airflow. Additional power may then be expended downstream of the photocatalyst to cool the airflow. In some applications, for example, an aircraft or other vehicle, any additional power usage may result in reduced fuel efficiency. In addition, weight may be added to the system if heavier or additional components, such as a larger fan, are necessary to accomplish the cooling. This may result in reduced cargo or passenger capacity.

Reducing the radiation of the UV-LEDs to the minimum level necessary to meet a desired contaminant reduction target may result in lower power consumption and lower airflow heat absorption. However, in some cases, when radiation levels are reduced, although the reduction target for some contaminants may be met, the concentration level of by-products produced in the oxidation process may exceed a desired level. For example, ethanol levels in airflow may be reduced through oxidation with a photocatalytic device. At lower radiation levels, however, the oxidation process may increase the concentration of acetaldehyde in the airflow to an unacceptable level. To additionally meet a desired target for by-product concentration, a higher power level may be needed than the power level necessary to only reduce the contaminant levels.

As can be seen, there may be an ongoing need for a system and/or method to reduce the concentration of contaminants and by-products in recirculated airflow at lower power levels.

SUMMARY OF THE INVENTION

In one aspect of the invention, an air purification system is disclosed comprising an airflow channel including an inlet and an outlet; a support disposed in the airflow channel; a photocatalyst on the support disposed to contact airflow through the airflow channel passing across or through the support; an ultraviolet light emitting diode disposed to emit ultraviolet light onto the photocatalyst; a power source selectively electrically connected to the ultraviolet light emitting diode to provide current to the ultraviolet light emitting diode at a duty cycle, the duty cycle in response to a duty cycle control signal; and a controller configured to generate the duty cycle control signal at least in part as a function of a desired minimum volatile organic compound conversion rate of air flowing through the airflow channel and a desired maximum by-product concentration in air flowing through the outlet of the airflow channel.

In another aspect of the invention, a method for purifying air is disclosed comprising directing air through an inlet of an airflow channel; determining a desired minimum volatile organic compound conversion rate of the air; determining a desired maximum by-product concentration in the air when it flows through an outlet of the airflow channel; generating with a controller, a power control signal indicative of a desired power duty cycle of an ultraviolet light emitting diode, the desired duty cycle determined, at least in part, as a function of the desired minimum VOC conversion rate and the desired maximum by-product concentration; powering the ultraviolet light emitting diode at the desired duty cycle, directing the air into contact with a photocatalyst, the photocatalyst disposed in the airflow channel; and irradiating the photocatalyst with ultraviolet light from the ultraviolet light emitting diode.

In a further aspect of the invention, an aircraft air purification system is disclosed comprising an aircraft cabin, an airflow channel including an inlet and an outlet, both the inlet and the outlet fluidly connected to the cabin; a support disposed in the airflow channel; a photocatalyst on the support disposed to contact airflow through the airflow channel passing across or through the support; an ultraviolet light emitting diode (UV-LED) disposed to emit ultraviolet light onto the photocatalyst; a power source selectively electrically connected to the UV-LED to provide current to the UV-LED at a duty cycle, the duty cycle in response to a duty cycle control signal; and a controller configured to generate the duty cycle control signal at least in part as a function of a desired minimum volatile organic compound (VOC) conversion rate of air flowing through the airflow channel and a desired maximum by-product concentration in air flowing through the outlet of the airflow channel.

BRIEF DESCRIPTION OF THE DRAWINGS

FIG. 3 is a chart showing a relationship between contaminant conversion, power, and by-product concentration in an air purification system according to an exemplary embodiment of the present invention;

FIG. 4 is a graphical representation of a duty cycle power input to a UV-LED according to an exemplary embodiment of the present invention;

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

Broadly, embodiments of the present invention provide an air purification system which may be used to remove contaminants from the cabin air of an aircraft or other enclosed space which uses recirculated air. By passing the air over a photocatalyst irradiated by UV-LEDs powered with a desired duty cycle, as opposed to a constant power or current supply, a minimum level of contaminant conversion may be achieved, without production of by-products above a desired concentration, and using less power than UV-LEDs operated with a constant power or current supply.

Figure 1:
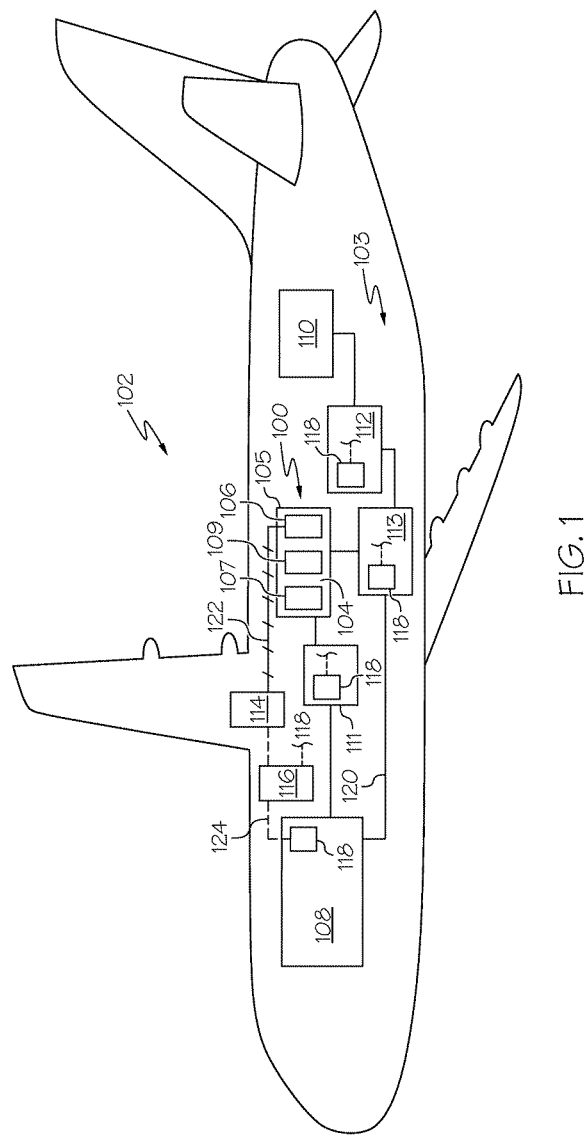
FIG. 1 is a schematic of an aircraft with an air purification system according to an exemplary embodiment of the present invention.

Referring now to FIG. 1, a schematic of an exemplary air purification system 100 in an exemplary aircraft 102 environment is illustrated. In the schematic, air conduits 120 may be represented by solid lines; communication links 124 may be represented by dashed lines, and power conductors 122 may be represented by hatched lines.

The aircraft 102 may include a cabin 108 for transporting passengers; engines 110 for motive and other power; and an air system 103 for providing breathable, pressurized air, in a desired temperature and humidity range, to the cabin 108. The engines 110 may include one or more compressors (not shown), and bleed air from the one or more compressors may be supplied to the air system 103, as is known in the art. The air system 103 may include an environmental control system (ECS) 112 to provide air to the cabin 108 in a desirable temperature and humidity range, as is well known in the art.

The air system 103 may include the air purification system 100 to remove contaminants from the air supplied to the cabin 108. The air purification system 100 may include an airflow channel 104. In some embodiments, the airflow channel 104 may include a chamber 106. Air may flow through air conduits 120 (including in some embodiments vents in the cabin floor), from the cabin 108 to a cargo hold 111. Air may flow from the cargo hold 111 into an air purification unit 105, which may include airflow channel 104 and chamber 106. The air purification unit 105 may also include other air purification devices as is known in the art. In the depicted exemplary embodiment, the air purification unit 105 may include a HEPA filter 107 and a carbon canister 109. Contaminants may be removed from the air as it flows through the chamber 106, and other air purification devices in air purification unit 105. Decontaminated air from the air purification unit 105 may flow into a mixing manifold 113. Bleed air from the engines 110 may flow into the ECS 112. The ECS 112 may provide air in a desired temperature, pressure, and humidity range to the mixing manifold 113, to mix with air from the air purification unit 105. Air from the mixing manifold 113 may then flow back to the cabin 108.

The air purification system 100 may include a power source 114, a controller 116, and one or more VOC (volatile organic compound) concentration feedback devices 118. The power source 114 may be electrically connected to provide power to the chamber 106 through power conductors 122. The power source 114 may include batteries or other sources of electric power (not shown), as well as power control devices such as switches (not shown). The VOC concentration feedback device 118 may generate VOC feedback signals indicative of a VOC concentration in the cabin 108 air, and may be located in the cabin 108, the cargo hold 111, the mixing manifold 113, the ECS 112, and/or in any other location which would be known in the art. The VOC concentration feedback device 118 may be communicatively linked to the controller 116 through communication links 124, to transmit the VOC feedback signals to the controller 116. The controller 116 may be configured to generate power control signals, and may be communicatively linked to power source 114 through communication links 124, to transmit the power control signals to power source 114.

The controller 116 may include a processor (not shown) and a memory component (not shown). The processor may include microprocessors or other processors as known in the art. In some embodiments the processor may include multiple processors. The controller 116 may execute instructions, as described below and in relation to FIG. 7, which includes determining a desired duty cycle for one or more UV-LEDs 136 (shown and described in relation to FIG. 2). A duty cycle (described in more detail in relation to FIG. 4) may provide pulsed power, alternating between a high power level and a low power level, as opposed to a constant power or current level to UV-LEDs 136. The controller 116 may execute instructions for determining the desired duty cycle for one or more UV-LEDs 136, at least in part, as a function of a desired minimum VOC conversion rate and a desired maximum by-product concentration. The controller 116 may generate the power control signals indicative of the desired duty cycle.

Such instructions may be read into or incorporated into a computer readable medium, such as a memory component, or provided external to processor. The instructions may include multiple lines or divisions of code. The lines or divisions of code may not be consecutive order, and may not be located in the same section of code. In alternative embodiments, hard-wired circuitry may be used in place of or in combination with software instructions to determine the desired duty cycle for one or more UV-LEDs 136. Thus embodiments are not limited to any specific combination of hardware circuitry and software.

The term "computer-readable medium" as used herein refers to any medium or combination of media that participates in providing instructions to the processor for execution. Such a medium may take many forms, including but not limited to, non-volatile media, volatile media, and transmission media. Non-volatile media includes, for example, optical or magnetic disks. Volatile media includes dynamic memory. Transmission media includes coaxial cables, copper wire and fiber optics.

Although the schematic of FIG. 1 illustrates the air purification system 100 in an aircraft 102 environment, it will be understood by those skilled in the art that the air purification system 100 is not limited to any one environment. For example, stationary environments with limited ventilation systems, or other motive environments, such as land vehicles, may also benefit from the inclusion of the air purification system 100.

Figure 2:
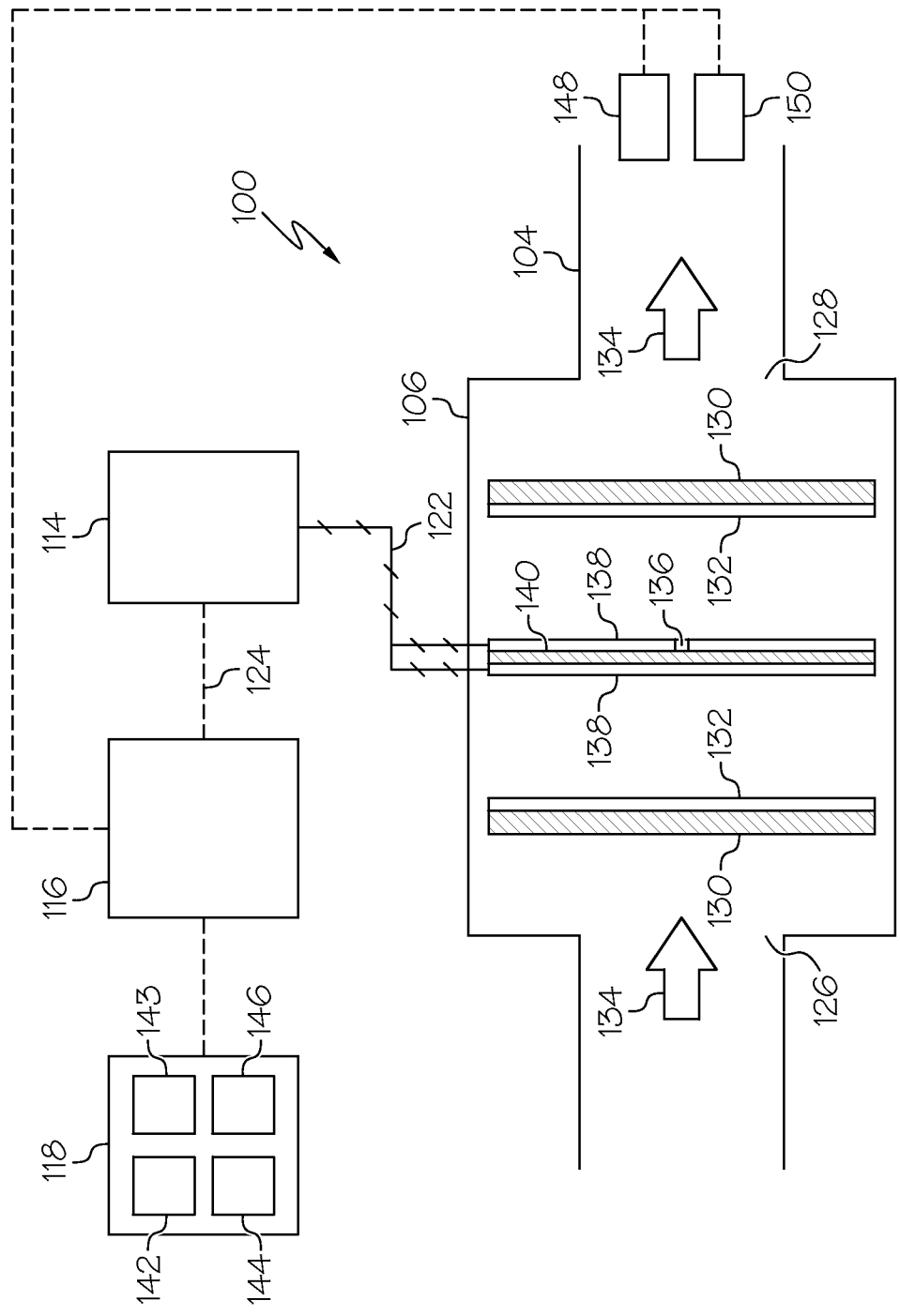
FIG. 2 is a schematic of an air purification system according to an exemplary embodiment of the present invention.

Referring now to FIG. 2, a more detailed schematic of the air purification system 100 is illustrated. The air purification system 100 may include a photocatalyst 132 and at least one UV-LED 136 disposed in the chamber 106. The photocatalyst 132 may be disposed on at least one photocatalyst support 130. Suitable photocatalyst supports 130 may include plates with apertures or perforations, a corrugated structure, or any other photocatalyst support 130 which would be known by an ordinary person skilled in the art. The photocatalyst 132 may include titanium oxide ($TiO_2$). Although depicted in the schematic as plates orthogonal to airflow (airflow is depicted by arrows 134) into the channel 104, the photocatalyst supports 130 coated with the photocatalyst 132, may take many forms as would be known by ordinary persons skilled in the art. For example, an annular configuration may be included in some embodiments. The photocatalyst 130 may be positioned in the airflow so that organic contaminants (not shown) in the airflow make contact with the photocatalyst 130.

The at least one UV-LED 136 may be positioned to emit ultraviolet light onto the photocatalyst 130 to produce a reaction between the photocatalyst 130 and the organic contaminants (not shown) in the airflow, converting the organic components to oxidation products such as carbon dioxide and water. The at least one UV-LED 136 may be part of an UV-LED array 138 positioned to emit ultraviolet light onto the photocatalyst 130. The UV-LED array 138 may be disposed on a UV-LED support 140, and may include multiple UV-LEDs 136 (although only one UV-LED 136 is shown in FIG. 2). The UV-LED support 140 may be designed to act as a heat sink and to dissipate heat produced by the UV-LED array 138. Although illustrated in plates orthogonal to the air flow through the airflow channel, the combined UV-LED support 140 and UV-LED array 138 may take on other forms as would be known to ordinary persons skilled in the art. The at least one UV-LED 136 may be powered by, and operatively connected to the power source 114 through power conductors 122.

The exact configuration of the photocatalyst supports 130 coated with the photocatalyst 132, and UV-LED supports 140 and UV-LED array may depend on numerous factors that will be known by ordinary persons skilled in the art. The physical geometry of the air system 103; the amount of airflow through the system; the power level, wavelength, current level supplied to and number of UV-LEDs, the desired contaminant reduction, and amount of non-recirculated air to be added to the recirculated air, are all non-limiting examples that may be considered.

Air to be decontaminated from areas such as the aircraft cabin 108, may flow through the cargo hold 111, into the air purification unit 105, and into an inlet 126 of the airflow channel 104 and come into contact with the catalyst 130. If ultra-violet light from the UV-LED array 138 is being emitted onto the photocatalyst 130, oxidation of contaminants (such as VOCs) may occur, resulting in a reduced concentration of contaminants flowing through the outlet 128 of the airflow channel 104.

It may be desirable to limit the amount of power provided to the UV-LED array 138 to a level such that a desired reduction of contaminants is achieved, but the minimum amount of heat is added to the airflow through airflow channel 104. Controlling the power supplied to the UV-LED array 138, may limit heating of the airflow. One or more VOC concentration feedback devices 118 may generate VOC feedback signals indicative of a contaminant level in air flowing into the airflow channel 104. The VOC concentration feedback device 118 may, for example, include a carbon dioxide ($CO_2$) sensor 142. In one exemplary embodiment, the $CO_2$ sensor 142 may be disposed in the cargo hold 111 and configured to generate $CO_2$ concentration signals. The amount of VOCs in cabin 108 air (and thus is the air vented into the cargo hold 111) may be approximated by the number of people in the cabin. The amount of $CO_2$ in the cabin 108 air may be indicative of the number of people in the cabin 108. The controller 116 may receive $CO_2$ concentration signals from the $CO_2$ sensor and may generate power control signals, at least in part, as a function of the $CO_2$ concentration signals.

In an alternative embodiment, the VOC concentration feedback device 118 may include a VOC concentration sensor 144, disposed in the air system 103, and configured to generate contaminant concentration signals indicative of a contaminant concentration. The VOC concentration sensor 144 may, for example, be disposed in the cargo hold 111, or the mixing manifold 113. The controller 116 may receive the contaminant concentration signals from the VOC contaminant concentration sensor 144 and may generate power control signals at least in part as a function of the contaminant concentration signals. The contaminant concentration sensor 144, for example, may sense the concentration of ethanol in air in the air system 103.

In another embodiment, the VOC concentration feedback device 118 may include an outside contaminant sensor 143, disposed in the ECS 112 or the mixing manifold 113, for example. The outside contaminant sensor 143 may be configured to generate bleed air contaminant concentration signals indicative of contaminants in the bleed air which entered the air system 103 from outside the aircraft 102. For example, contaminants from adjacent aircraft or other pollutants may be sensed. The controller 116 may receive the contaminant concentration signals from the outside contaminant sensor 143 and may generate power control signals at least in part as a function of the contaminant concentration signals.

In another embodiment, the VOC concentration feedback device 118 may include a data input device 146. The data input device 146 may be disposed in the cabin 108. Flight personnel may be able to enter data indicative of VOC concentration in cabin 108 air into the data input device 146. For example, the number of people in the cabin may be inputted. Aromas sensed by the human nose may be another VOC concentration indicator. The data input device 146 may allow the entry, by an operator (such as a flight attendant or other crew member), of data indicative of a level of odor which may be offensive to passengers and/or crew. The data input device 146 may, for example, include a keypad, a dial, buttons, voice recognition, or other input interfaces (not shown) as are known in the art. The controller 116 may receive the data inputted into the data input device 146 and may generate power control signals at least in part as a function of the data.

It may be desirable to operate the UV-LED array with the minimum amount of power needed to reach a desired contaminant conversion, and thus increase power efficiency and reduce the amount of thermal energy added to airflow. However, in some conditions, by-products may be produced in the conversion process at unacceptable levels when lower power levels are used.

In some embodiments, the air purification system 100 may include a temperature sensor 148 disposed to monitor the temperature of air flowing from the outlet 128. The temperature sensor 148 may be disposed at the outlet 128 or downstream of the outlet 128 as would be known in the art. The temperature sensor 148 may generate temperature signals indicative of the temperature of the air flowing from outlet 128. Air exiting the air purification unit 105 may mix with air from the ECS 112 in the mixing manifold 113 and return to the cabin 108. If the UV-LED array is operated at too high a power level (the power level depending on the application and operating environment), the air entering the cabin 108 may be at a higher temperature than is comfortable for passengers and crew members. The temperature sensor 148 may be communicatively connected to the controller 116, and the controller 116 may receive the temperature signals and may generate power control signals at least in part as a function of the temperature signals.

In some embodiments the air purification system 100 may include a by-product sensor 150 disposed to monitor the concentration of by-products in the air flowing from the outlet 128. The by-products may have been produced by the photocatalyst 132. The by-product sensor may be disposed at the outlet 128 or downstream of the outlet 128 as would be known in the art. The by-product sensor 150 may generate by-product concentration signals indicative of the concentration of by-products in the air flowing from the outlet 128. The by-product concentration sensor 150 may be communicatively connected to the controller 116, and the controller 116 may receive the by-product concentration signals and may generate power control signals at least in part as a function of the by-product concentration signals. In one exemplary embodiment, the by-product concentration sensor 150 may monitor the concentration of acetaldehyde in the air flowing from the outlet 128.

Referring now to FIG. 3, a chart 200 showing a relationship between contaminant conversion, power, and by-product concentration in the air purification system 100 is illustrated. Data gathered using modeling and simulation techniques for an exemplary air purification system 100 may have been used to create the chart 200. Models based on simple Gaussian distribution may have been used to produce the data. Ethanol may have been used as an exemplary contaminant, and acetaldehyde may have been used as an exemplary by-product in the modeling and simulation. The modeling and simulation used to create chart 200 may have assumed that a constant UV-LED 136 power (or current) level was provided to the UV-LEDs 136.

The x-axis 202 represents the percentage of VOC conversion achieved. The percentage of VOC conversion 202 is plotted against power expended in powering the UV-LEDs 136 on a primary y-axis 204 (solid line left-side y-axis); and by-product concentration in airflow leaving the air purification system 100 on a secondary y-axis 206 (dashed line right-side y-axis). Data points and solid connecting line 208 may represent the percentage of VOC conversion achieved (x axis) when expending an amount of power (primary y axis) for different power level UV-LEDs 136. For example, the data points may have plotted for a 5 W, 7 W, 10 W, 15 W, 18 W, and 25 W UV-LED 136. These data points may then have been connected with the solid line 208. Solid line 212 may represent a minimum target or desired percentage of VOC conversion. Points to the right of solid line 212 meet the target or desired minimum VOC conversion. The minimum target or desired percentage of conversion may, for example, be fifty percent (50%). The star 216 represents the minimum power 204 that must be expended to reach the minimum target or desired conversion of VOCs.

Data points and dashed connecting line 222 represent the percentage of VOC conversion verses outlet concentration of by-products for different power level UV-LEDs 136. As with plot 208, the data points may be plotted for a 5 W, 7 W, 10 W, 15 W, 18 W, and 25 W UV-LED 136. The line 222 may connect the data points. Dashed line 214 may represent a maximum target or desired concentration of outlet by-products. Points under the dashed line 214 meet the target or desired concentration of outlet by-products. The maximum target or desired concentration of by-products may, for example, be eighty-five (85) parts per billion (ppb). To meet both the minimum target or desired VOC conversion as well as the maximum desired outlet concentration of by-products, a point on the percentage of VOC conversion verses outlet concentration of by-products plot 210 must be to the right on line 212 and under line 214. The striped rectangle 218 represents the corresponding power levels of points which meet this criteria.

Those skilled in the art may recognize that although the minimum desired VOC conversion percentage may have been met at power level 216, an increased power level was necessary to simultaneously meet the maximum desired outlet by-product concentration level.

Mercury vapor bulbs have been used in the prior art to emit ultra-violet light onto a photocatalyst to reduce contaminants in airflow. A drawback to control of the level of ultra-violet light emitted by mercury vapor bulbs is their delay in responding to changes in current levels. UV-LEDs, however, may respond quickly to current changes allowing them to be rapidly switched on and off in response to a duty cycle power input.

Referring now to FIG. 4, a graphical representation of a power signal 300 to a UV-LED 136 being operated with a duty cycle is illustrated. For practical purposes, when operating in a duty cycle, the power signal 300 may alternate between a high (sometimes referred to as on or full current) and a low (sometimes referred to as an off or no current) level. Although at very high switching rates, a delay may be perceived in the signal, at the speed that switching may occur for operation in the air purification system 100, the delay may be negligible. The height 302 of the power signal 300 may represent the power or current magnitude being supplied to the UV-LED 136 when the power signal 300 is at a high (or on) level. The width 308 may represent the period of the duty cycle, and for the purposes of this application may be the time it takes for a signal to complete a high and low (on and off) cycle. The width 304 may represent the time period in which the power signal 300 is at a high level during a period. The width 306 may represent the time period the power signal 300 is at a low level during a period. For the purposes of this application, the frequency of a duty cycle may be the number of periods of a duty cycle during a predetermined time period 310. For example, in the illustrated embodiment the frequency may be the number of time periods 308 per time period 310. For the purposes of this application, a duty cycle may be defined as the percentage of one period 308 in which a power signal is at a high level. In the illustrated example, the duty cycle may be the time period 304 divided by the time period 308 multiplied by one hundred (100).

Prior photo-catalyst air purification systems with mercury vapor lamps have been limited to supplying ultra-violet light at a constant radiation level. Although photo-catalyst air purification systems with UV-LEDs are known, they may have been limited in the past to operating the UV-LEDs 136 at a constant power or current level. Modeling and simulation data may show a relationship between the power level supplied to UV-LEDs 136 at a constant power or current level and the level of by-products produced by oxidation with a photocatalyst 130; and that as the level of power supplied to the UV-LEDs 136 is increased, the level of by-product production is decreased. The data may also show that the percentage of VOCs converted in the photocatalyst oxidation process increases with the level of power supplied to UV-LEDs 136. The data may also show that the power level needed to reach a desired conversion of VOCs with UV-LEDs 136 supplied with a constant power or current level is lower than the power level needed to decrease the by-product concentration to a desired level. Data generated by models of photocatalyst air purification systems with UV-LEDs 136 operated at a duty cycle less than 100% may indicate that it may be possible to meet the desired VOC conversion and by-product concentration level at a lower average power level.

Figure 5:
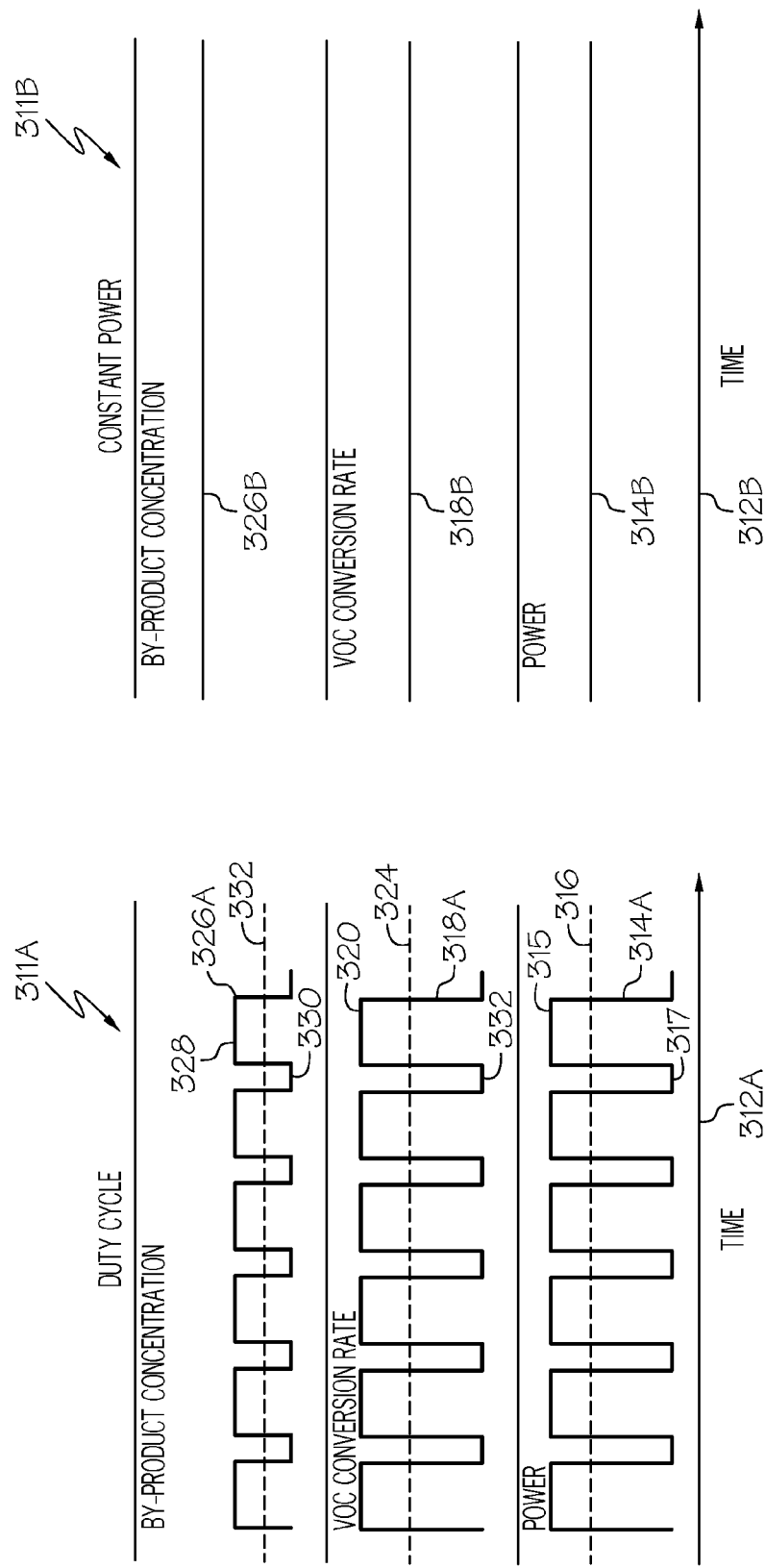
FIG. 5 is two side-by-side graphical representations of power (or current) supplied to UV-LEDs, resultant VOC conversion, and resultant by-product concentration according to an exemplary embodiment of the present invention.

Referring now to FIG. 5, side-by-side graphical representation and comparison of power (or current) supplied to UV-LEDs 136, resultant VOC conversion, and resultant by-product concentration as a function of time for both a 100% duty cycle and a lower than 100% duty cycle are illustrated. Chart 311A may be a graphical representation of the power (or current) supplied to UV-LEDs 136 (plot 314A), resultant VOC conversion (plot 318A), and resultant by-product concentration (plot 326A) as a function of time (axis 312A) for a less than 100% duty cycle. Chart 311B may be a graphical representation of the power (or current) supplied to UV-LEDs 136 (plot 314B), resultant VOC conversion (plot 318B), and resultant by-product concentration (plot 326B) as a function of time (axis 312B) for a 100% duty cycle.

In chart 311A, the high power portions of the duty cycle 315, and the low power portions of the duty cycle 317, supply an average power to the UV-LEDs 136 represented by the dashed line 316. The average power supplied at less than 100% duty cycle (and represented by line 316) may be equal to the constant power supplied by a 100% duty cycle (represented by line 314B).

In the chart 311A plot of VOC conversion 318A, when the duty cycle has high power, there may be a high VOC conversion rate 320. When the duty cycle has low power, there may be a low (or zero) VOC conversion rate 322. The average VOC conversion rate is represented by dashed line 324, and may be equal to the chart 311B conversion rate (represented by 318B) accomplished with a 100% duty cycle.

In the chart 311A plot of by-product production 326A, when the duty cycle has high power, there may be a non-zero by-product concentration 328. When the average power level (316) supplied to UV-LEDs in a less than 100% duty cycle is equal to the constant power level (314B) supplied in a 100% duty cycle, the power level (315) supplied to the UV-LEDs 136 during the high portion of the less than 100% duty cycle will be higher than the constant power level (314B) supplied to the UV-LEDs 136 during the 100% duty cycle. Since data suggests that the by-product concentration decreases as the power level supplied to UV-LEDs 136 increases, the byproduct concentration 328 during the high portion of a less than 100% cycle may be less than the by-product concentration 326B during a 100% duty cycle. In the chart 311A plot of by-product concentration, when the duty cycle has low power, there may be a zero by-product concentration 330. The resultant average by-product concentration is represented by dashed line 332, and may be much lower than the by-product concentration 326B produced in a 100% duty cycle with the same average power expenditure. Thus, by operating UV-LEDs 136 in the air purification system 100 in a less than 100% duty cycle, it may be possible to achieve a desired minimum VOC conversion rate and a desired maximum by-product concentration using less power than would be necessary if the UV-LEDs 136 were operated at a 100% duty cycle.

Figure 6:
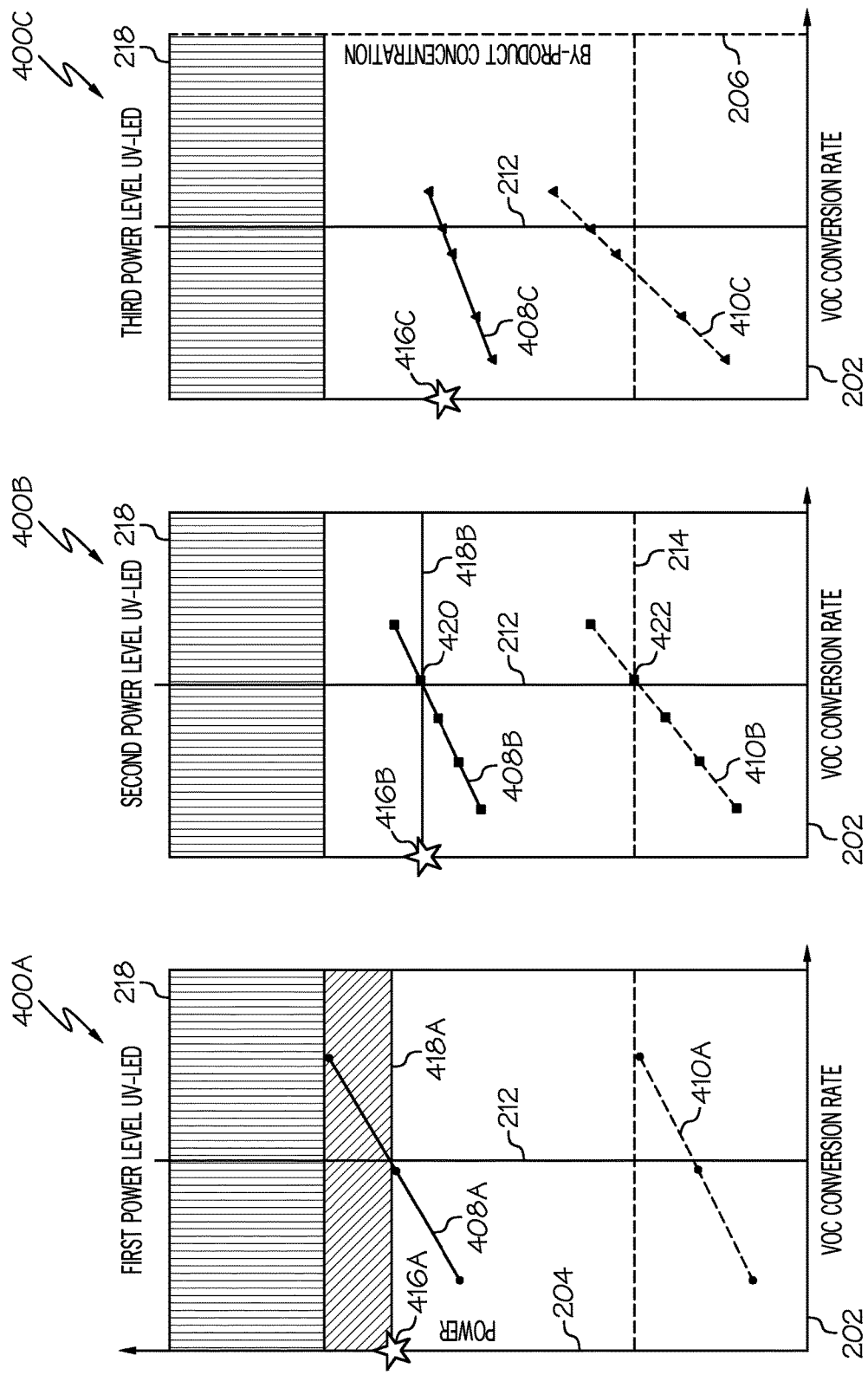
FIG. 6 is three side-by-side charts showing relationships between contaminant conversion, power, and by-product concentration in an air purification system according to an exemplary embodiment of the present invention.

Referring now to FIG. 6, side-by-side charts 400 showing relationships between contaminant conversion, power, and by-product concentration in the air purification system 100 when operating three different power level UV-LEDs 136 at different duty cycles are illustrated. Data to create the charts 400 may have been gathered in a similar manner as the data used to create the chart 200 in FIG. 3. Chart 400A may have been created with data relating to a 15 W UV-LED 136 operated at a 33%, 66%, and 100% duty cycle. Chart 400B may have been created with data relating to a 10 W UV-LED 136 operated at a 33%, 50%, 66%, 80%, and 100% duty cycle. Chart 400A may have been created with data relating to a 7.5 W UV-LED 136 operated at a 33%, 50%, 75%, 85% and 100% duty cycle.

As in FIG. 3, the x-axes 202 may represent the percentage of VOC conversion achieved. The primary y axis 204 may represent the average power expended in powering the UV-LED 136, and the secondary y axis may represent the by-product concentration in airflow leaving the air purification system 100. Solid line 212 may represent a minimum desired percentage of VOC conversion, and dashed line 214 may represent a maximum desired concentration of outlet by-products. The striped rectangle 218 represents the band of power levels from FIG. 3 which met the desired minimum VOC conversion level and the desired maximum by-product concentration level when operating the UV-LEDs 136 at a 100% duty cycle. These power bands 218 are included for comparison reasons.

Data points and solid connecting lines 408A, 408B, and 408C may be plots of VOC conversion verses average power to the UV-LEDs 136 at different duty cycles. Points to the right of solid line 212 may meet the minimum desired VOC conversion rate. Data points and dashed connecting lines 410A, 410B, and 410C may be plots of VOC conversion verses by-product concentration plotted for UV-LEDs 136 operated at different duty cycles. Points under the dashed line 214 may meet the desired maximum by-product concentration. Stars 416A, 416B, and 416C show the minimum power level at which the UV-LED 136 met the minimum VOC conversion rate. Diagonally striped rectangle 418A and line 418B represent power levels at which the UV-LED 136 being plotted met both the minimum desired VOC conversion rate, and the maximum desired by-product concentration.

It may be recognized by those skilled in the art, that the UV-LEDs 136 for which data was plotted in charts 400A and 400B may be able to meet the desired minimum VOC conversion rate and the desired maximum by-product concentration when operated at a less than 100% duty cycle at an average power level below the power level required to meet the same desired targets when operating a UV-LED at 100% duty cycle. The UV-LED 136 for which data was plotted in 400C may not be able to meet the targets in the air purification system 100 modeled to gather the data used in creating the chart.

In one exemplary embodiment, the UV-LED 136 for which data was charted in chart 400B may be a 10 W UV-LED 136. The points charted may be at duty cycles of 33%, 50%, 66% 80%, and 100%. The minimum VOC conversion rate target 212 may be 50%, and the maximum by-product concentration target 214 may 85 ppb. The VOC conversion rate at the 80% duty cycle may be represented at point 420, and may be 51.10%. The by-product concentration at the 80% duty cycle may be represented by point 422 and may be 85 ppb. Total power at the 80% duty cycle may be 1.45 kW. Data from the same model for several different powered UV-LEDs 136 supplied with constant power or current may be shown in chart 200 in FIG. 3. The points charted may be for a 5 W, a 7 W, a 10 W, a 15 W, an 18 W, and a 25 W UV-LED. The minimum VOC conversion rate target 212 may be 50%, and the maximum by-product concentration target 214 may 95 ppb, similar to chart 400B. The lowest power UV-LED 136 to meet both the minimum VOC conversion rate, and the maximum by-product concentration may be the 15 W UV-LED 136, with a 71.10% VOC conversion rate at points 220 and 222, and a 93 ppb by-product concentration at point 222. Total power for the 15 W UV-LED 136 may be 2.73 kW (at point 220), much higher than the 1.45 kW needed to run a 10 W UV-LED at an 80% duty cycle.

The relationships illustrated in the charts in FIGS. 3 and 6, along with additional experimental, modeled, and simulation data for the air purification system 100 may be used to specify a power level, configuration, and wavelength of the UV-LEDs 136 included in the air purification system 100. As will be apparent to those skilled in the art, the specific geometry, application, and other characteristics of the air purification system 100 may impact the decision as well. Once design specifications are chosen, data on the relationships between duty cycle and frequency of the UV-LEDs 136, the VOC conversion rates, the by-product concentration rates, and the minimum power levels necessary to achieve a desired minimum VOC conversion rate and a maximum by-product concentration may be stored in the memory of the controller 116 for use in determining and generating power control signals. This data may be in the form of look-up tables, algorithms, or other forms of stored data as would be known by those skilled in the art.

Figure 7:
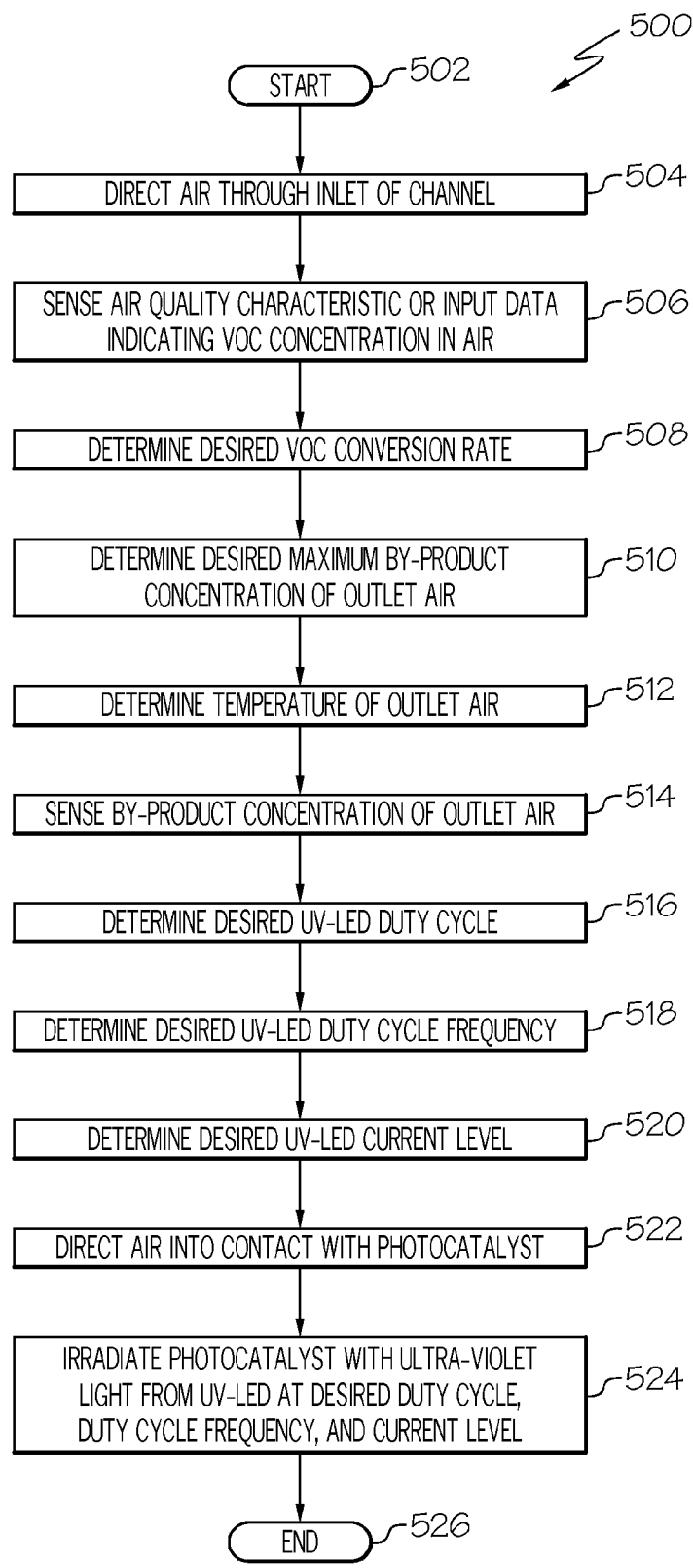
FIG. 7 is a flow chart illustrating a method for purifying air according to an exemplary embodiment of the present invention.

Referring now to FIG. 7, a flow chart depicting a method 500 for purifying air is illustrated. The method may start at 502. In step 504 air may be directed through the inlet 126 of the airflow channel 104. In one embodiment, the air may be directed from the cabin 108 of an aircraft 102, through the cargo hold 111, into the air purification unit 105, and into the airflow channel 104.

In step 506, an air quality characteristic may be sensed by, or data indicative of an air quality characteristic may be inputted into a VOC concentration rate feedback device 118. In one exemplary embodiment, the VOC concentration feedback device 118 may include a $CO_2$ sensor 142 located in the cargo hold 111 or the cabin 108 of the aircraft 102. The $CO_2$ sensor 142 may generate a $CO_2$ concentration signal indicative of the level of $CO_2$ concentration in the cabin 108 air. In an alternative embodiment, the VOC concentration feedback device 118 may include a VOC concentration sensor 144 located in the air system 103 of the aircraft 102. The VOC concentration sensor 144 may generate a VOC concentration signal indicative of the level of VOC concentration in the airflow entering the inlet 126 of the airflow channel 104. In another embodiment, the VOC concentration feedback device 118 may include a data input device located in the cabin 108 of the aircraft 102. Air quality data indicative of an air quality characteristic may be inputted by an operator into the data input device. For example, an operator may input data indicating the number of passengers and crew members in the cabin 108; or alternatively the operator may input data indicating an odor level in the cabin air. In another embodiment the VOC concentration feedback device may include the outside contaminant sensor disposed in the ECS 112 or the mixing manifold 113.

In step 508, a desired minimum VOC conversion rate may be determined by the controller 116. The desired minimum VOC conversion rate may be determined, at least in part, from the air quality characteristic sensed or inputted. The desired minimum VOC conversion rate may also be determined, at least in part, by a predetermined desired VOC minimum conversion rate stored in the memory which may be adjusted based on feedback signals from the VOC concentration feedback device 118. The predetermined desired VOC conversion rate may be the result of experimental data and/or air system 103 design.

In step 510, a desired maximum by-product concentration of air flowing through the outlet 128 of the airflow channel 104 may be determined by the controller 116. The desired maximum by-product concentration may be determined, at least in part, by a predetermined desired maximum by-product concentration stored in the controller 116. The predetermined value may be based on experimental data and/or air system 103 design. The predetermined value may be adjusted based on feedback signals from the VOC concentration feedback device 118.

In step 512, the temperature of the air flowing through the outlet 128 may be determined with the temperature sensor 148. If the UV-LEDs 136 are operated at too high a power level, air flowing from the air purification system 100 back to the cabin 108 may be at a temperature too high for passenger and crew comfort.

In step 514, the by-product concentration of the air flowing through the outlet 128 may be determined with the by-product concentration sensor 150.

In step 516, a desired UV-LED 136 duty cycle may be determined by the controller 116. The desired UV-LED 136 duty cycle may be determined, at least in part, as a function of the desired minimum VOC conversion rate, the desired maximum by-product concentration, the temperature of and by product concentration in air flowing through outlet 128, and minimizing the power needed to operate the UV-LEDs 136. The controller 116 may utilize look-up tables, algorithms, or other methods stored in the memory to determine the desired UV-LED 136 duty cycle.

In step 518, a desired UV-LED 136 duty cycle frequency may be determined by the controller 116. The desired UV-LED 136 duty cycle frequency may be determined, at least in part, as a function of the desired minimum VOC conversion rate, the desired maximum by-product concentration, the temperature of and by product concentration in air flowing through outlet 128, and minimizing the power needed to operate the UV-LEDs 136. The controller 116 may utilize look-up tables, algorithms, or other methods stored in the memory to determine the desired UV-LED 136 duty cycle frequency. The UV-LED 136 duty cycle frequency may be in a range where the low end is above a point where the UV-LEDs would experience delays in switching, and below a point where humans in an aircraft cabin would notice a fluctuation of air having and not having an odor.

step 520, a desired UV-LED 136 duty cycle current level may be determined by the controller 116. The desired UV-LED 136 current level may be determined, at least in part, as a function of the desired minimum VOC conversion rate, the desired maximum by-product concentration, the temperature of and by product concentration in air flowing through outlet 128, and minimizing the power needed to operate the UV-LEDs 136. The controller 116 may utilize look-up tables, algorithms, or other methods stored in the memory to determine the desired UV-LED 136 current level.

In step 522, airflow may be directed into contact with the photocatalyst 130. In step 524 the photocatalyst may be irradiated with ultra-violet light from the UV-LEDs 136 being operated at the desired duty cycle, the desired duty cycle frequency, and the desired current level. The radiation may cause the photocatalyst 130 to oxidize the desired percentage of VOCs in the airflow, and produce by-products below the maximum desired by-product concentration. The method may end at 526.

It should be understood, of course, that the foregoing relates to exemplary embodiments of the invention and that modifications may be made without departing from the spirit and scope of the invention as set forth in the following claims.

We claim:

1. A system for converting volatile organic compounds (VOC) in an airflow, comprising:
    an airflow channel including an inlet and an outlet;
    a support disposed in the airflow channel;
    a photocatalyst on the support disposed to contact airflow through the airflow channel passing across or through the support;
    an ultraviolet light emitting diode disposed to emit ultraviolet light onto the photocatalyst;
    a power source selectively electrically connected to the ultraviolet light emitting diode to provide current to the ultraviolet light emitting diode at a duty cycle, the duty cycle in response to a duty cycle control signal;
    a VOC concentration feedback device; and
    a controller having a memory that correlates VOC conversion rate with concentration of organic by-products of the VOC conversion at various duty cycles,
    wherein the controller is configured to generate the duty cycle control signal at least in part as a function of a target VOC conversion rate in air flowing through the airflow channel, and a non-zero target concentration of the organic by-products of said VOC conversion in air flowing out of the airflow channel.

2. The system of claim 1, wherein the volatile organic compound concentration feedback device includes a carbon dioxide sensor, and an air quality feedback signal includes a carbon dioxide concentration signal indicative of a concentration of carbon dioxide in the air flowing into the inlet of the airflow channel.

3. The system of claim 1, wherein the volatile organic compound feedback device includes a volatile organic compound sensor, and an air quality feedback signal includes a signal indicative of the concentration of at least one particular volatile organic compound in the air flowing into the inlet of the airflow channel.

4. The system of claim 1, wherein the volatile organic compound feedback device includes a user input device for inputting an air quality feedback signal.

5. The system of claim 4, wherein the user input device is configured to accept input from a user indicative of a number of passengers in an aircraft cabin or a level of odor in the cabin air.

6. The system of claim 1, further comprising a temperature sensor configured to generate a temperature signal indicative of a temperature of air flowing through the outlet of the airflow channel, and
    wherein the controller is configured to generate the duty cycle control signal at least in part as a function of the temperature signal.

7. The system of claim 1, wherein the power source is configured to provide current to the ultraviolet light emitting diode at the duty cycle, at a frequency and a current level, the frequency as a response to a duty cycle frequency control signal, the current level as a response to a duty cycle current level control signal, and wherein the controller is configured to generate the duty cycle frequency control signal and the current level control signal, at least in part, as a function of the target VOC conversion rate in air flowing through the airflow channel and the target concentration of the organic by-products of said conversion in air flowing through the outlet of the airflow channel.

8. The system of claim 1, further comprising an array of ultraviolet light emitting diodes disposed to emit ultraviolet light onto the photocatalyst.

9. A method for converting volatile organic compounds (VOC) in an airflow, comprising:
    directing air through an airflow channel;
    determining a target conversion rate of VOC in the air;
    determining a non-zero target concentration of organic by-products of said conversion in the air;
    generating with a controller, a power control signal indicative of a power duty cycle of an ultraviolet light emitting diode, the duty cycle determined, at least in part, as a function of the target VOC conversion rate and the target organic by-product concentration;
    powering a ultraviolet light emitting diode at the duty cycle;
    directing the air into contact with a photocatalyst, the photocatalyst disposed in the airflow channel;
    irradiating the photocatalyst with ultraviolet light from the ultraviolet light emitting diode; and
    adjusting the power control signal to reduce the duty cycle if air emerging from the airflow channel has a concentration of the organic by-products lower than the non-zero target concentration, so that the power applied to the ultraviolet light emitting diodes is minimized.

10. The method of claim 9, further comprising;
    sensing an air quality characteristic indicative of the concentration of volatile organic compounds in the air flowing into the inlet of the airflow channel, and
    determining the duty cycle of the ultraviolet light emitting diode at least in part as a function of the air quality characteristic.

11. The method of claim 9, further comprising;
    inputting volatile organic compound concentration determination data indicative of the concentration of volatile organic compounds in the air flowing into the inlet of the airflow channel into a user input device, and
    determining the duty cycle of the ultraviolet light emitting diode at least in part as a function of the volatile organic compound concentration determination data.

12. The method of claim 9, wherein the air is directed from a cabin of an aircraft through the inlet of the airflow channel; and
    further comprising;
    sensing concentration of carbon dioxide in air in the cabin, and
    determining a desired duty cycle of the ultraviolet light emitting diode at least in part as a function of the concentration of carbon dioxide.

13. The method of claim 9, further comprising;
    determining a frequency of the duty cycle of the ultraviolet light emitting diode at least in part as a function of the target volatile organic compound conversion rate and the target by-product concentration; and
    irradiating the photocatalyst with ultraviolet light from the ultraviolet light emitting diode at the duty cycle at the determined frequency.

14. The method of claim 9, further comprising;
determining a current level to supply the ultraviolet light emitting diode at least in part as a function of the target VOC conversion rate and the target organic by-product concentration; and
supplying the ultraviolet light emitting diode with current at the determined current level.

15. The method of claim 9, wherein the air is directed through the inlet of the airflow channel from an aircraft cabin, and further comprising directing air from the airflow channel into the aircraft cabin.

16. A system for converting volatile organic compounds (VOC) in an aircraft, comprising:
an aircraft cabin,
an airflow channel including an inlet and an outlet, both the inlet and the outlet fluidly connected to the cabin;
a support disposed in the airflow channel;
a photocatalyst on the support disposed to contact airflow through the airflow channel passing across or through the support;
an ultraviolet light emitting diode disposed to emit ultraviolet light onto the photocatalyst;
a power source selectively electrically connected to the ultraviolet light emitting diode to provide current to the ultraviolet light emitting diode at a duty cycle at a frequency low enough to permit the ultraviolet light emitting diode to fully complete high to low cycles; and
a controller configured to generate the duty cycle control signal at least in part as a function of a target VOC conversion rate in air flowing through the airflow channel and a target concentration of organic by-products of conversion of VOC in air flowing through the outlet of the airflow channel.

17. The system of claim 16,
further comprising a volatile organic compound concentration sensor configured to generate a cabin air quality feedback signal indicative of a concentration of volatile organic compounds in air in the cabin;
and wherein the controller is configured to generate the duty cycle control signal at least in part as a function of the cabin air quality feedback signal.

18. The system of claim 16,
further comprising a volatile organic compound concentration user input device configured for inputting cabin air quality data indicative of the concentration of volatile organic compounds in air in the cabin;
and wherein the controller is configured to generate the duty cycle control signal at least in part as a function of the cabin air quality data.

* * * * *